(12) United States Patent
Aiyama

(10) Patent No.: US 7,051,949 B2
(45) Date of Patent: May 30, 2006

(54) VOLATILIZING APPARATUS

(75) Inventor: Kazushige Aiyama, Kasukabe (JP)

(73) Assignee: Sumitomo Chemical Company, Limited, Osaka (JP)

( * ) Notice: Subject to any disclaimer, the term of this patent is extended or adjusted under 35 U.S.C. 154(b) by 141 days.

(21) Appl. No.: 10/743,788

(22) Filed: Dec. 24, 2003

(65) Prior Publication Data

US 2004/0134999 A1    Jul. 15, 2004

(30) Foreign Application Priority Data

Dec. 24, 2002   (KR) ............................ 2002-0083279
Dec. 25, 2002   (JP) ............................ P2002-374901

(51) Int. Cl.
  *A24F 25/00*   (2006.01)
  *A61L 9/04*    (2006.01)
(52) U.S. Cl. ............................ 239/53; 239/34; 239/36; 239/37; 239/38; 239/41; 239/42; 239/43
(58) Field of Classification Search ................... 239/34, 239/36, 37, 38, 41, 42, 43, 44, 47, 51.5, 53–57
  See application file for complete search history.

(56) References Cited

U.S. PATENT DOCUMENTS

| 4,220,281 | A | * | 9/1980 | Martens et al. ................ 239/57 |
| 5,078,296 | A | * | 1/1992 | Amidzich .................... 220/838 |
| 5,297,732 | A | * | 3/1994 | Hahn ........................... 239/55 |
| 5,324,490 | A | * | 6/1994 | Van Vlahakis et al. ...... 422/305 |
| 5,610,359 | A | * | 3/1997 | Spector et al. ............... 89/1.11 |
| 5,935,526 | A | * | 8/1999 | Moore ........................ 422/124 |
| 6,327,813 | B1 |   | 12/2001 | Ishiwatari |

FOREIGN PATENT DOCUMENTS

| EP | 0 792 581   | 9/1997 |
| JP | 9-308421    | 12/1997 |
| JP | 11-322504   | 11/1999 |
| JP | 2000-189032 | 7/2000 |

* cited by examiner

*Primary Examiner*—Davis Hwu
(74) *Attorney, Agent, or Firm*—Wenderoth, Lind & Ponack, L.L.P.

(57) ABSTRACT

A volatilizing apparatus for volatilizing a volatile agent, includes: a container having a container body and a lid covering the container body. The lid is attached to the container body through a hinge member so as to open and close with respect to the container body. One end of a volatilizing body is fixed to the inner face of the container body, and the other end of the volatilizing body is fixed to the inner face of the lid. The volatilizing body has a laminated honeycomb structure, holds the volatile agent, and is adapted to be contained in the container under a closed state of the lid and to expand between the container body and the lid under an open state of the lid.

10 Claims, 11 Drawing Sheets great VOLATILIZING APPARATUS

BACKGROUND OF THE INVENTION

The present invention relates to a volatilizing apparatus for volatilizing a volatile agent such as a deodorant, an aromatic agent, a pesticide, an insecticide, a fungicide, a fresh-keeping agent, etc.

EP-792581 discloses a volatilizing body that has a laminated honeycomb structure and holds an insecticide. However, since the above volatilizing body is not contained in a container and can be only changed into an open state, there is a risk that a user will touch the insecticide.

JP11-322504A and JP2000-189032A disclose a volatilizing body having a protection layer. The protection layer prevents the user from touching the insecticide directly. However, when the above volatilizing body is changed into the open state, the user must catch supporting plates at both ends of the volatilizing body. Therefore, it is difficult for the user to operate the volatilizing body.

SUMMARY OF THE INVENTION

A main object of the present invention is to provide a volatilizing apparatus that can be handled safely and easily without a user's touching the volatile agent held on a volatilizing body.

The present invention provides a volatilizing apparatus for volatilizing a volatile agent. According to a first aspect of the present invention, the volatilizing apparatus comprises a container comprising a container body and a lid covering the container body, and a volatilizing body. The lid is attached to the container body through a hinge member so as to open and close with respect to the container body. One end of the volatilizing body is fixed to the inner face of the container body, and the other end of the volatilizing body is fixed to the inner face of the lid. The volatilizing body has a laminated honeycomb structure and holds the volatile agent. The volatilizing body is adapted to be contained in the container under the closed state of the lid and to expand between the container body and the lid under the open state of the lid.

According to the first aspect, a user can operate and open the volatilizing apparatus by catching the container body and the lid. That is, the user can use the volatilizing apparatus without touching the volatile agent held on the volatilizing body. Therefore, the volatilizing apparatus can be handled safely.

According to a second aspect of the present invention, the hinge member includes an energizing means for energizing the lid in a direction in which it opens from the container body. And the container includes a locking tool for locking the lid in the closed state to the container body.

According to the second aspect, the lid is opened automatically by the energizing means when the user disengages the locking tool. Therefore, the volatilizing apparatus can be handled easily.

According to a third aspect of the present invention, the energizing means is a spring installed so as to store an elastic force in the closed state of the lid.

According to the third aspect, the energizing means can be made simply.

According to a fourth aspect of the present invention, the energizing means is set to open the lid in a range from 230 degrees to 330 degrees with respect to the container body.

According to the fourth aspect, the following effects (i), (ii), and (iii) can be obtained.

(i) The open area of the volatilizing body becomes large. Therefore, the volatile agent can be volatilized effectively from the volatilizing body.

(ii) The volatilizing body expands in an arc. Therefore, the decorative effect of the volatilizing body can be improved.

(iii) The volatilizing apparatus is supported in a standing condition by the open container body. Therefore, the setting area of the volatilizing apparatus can be made small and the decorative effect of the volatilizing body can be improved.

According to a fifth aspect of the present invention, the locking tool comprises a locking piece formed at the lid and an engaging part formed at the container body for engaging with the locking piece. And the engaging part is adapted to disengage the locking piece from an engaged state by being pressed.

According to the fifth aspect, the locking tool can be made simply.

According to a sixth aspect of the present invention, the volatile agent is at least one selected from deodorant, aromatic agent, insecticide, pesticide, fungicide, and fresh-keeping agent.

According to the sixth aspect, the volatilizing apparatus can meet various requirements.

According to a seventh aspect of the present invention, the volatilizing body is provided with a cover body. The cover body has a laminated honeycomb structure and covers the upper part or the side part of the volatilizing body.

According to the seventh aspect, the cover body can prevent the user from touching the upper part or the side part of the volatilizing body. Therefore, the volatilizing apparatus can be handled more safely.

DETAILED DESCRIPTION

Figure 1:
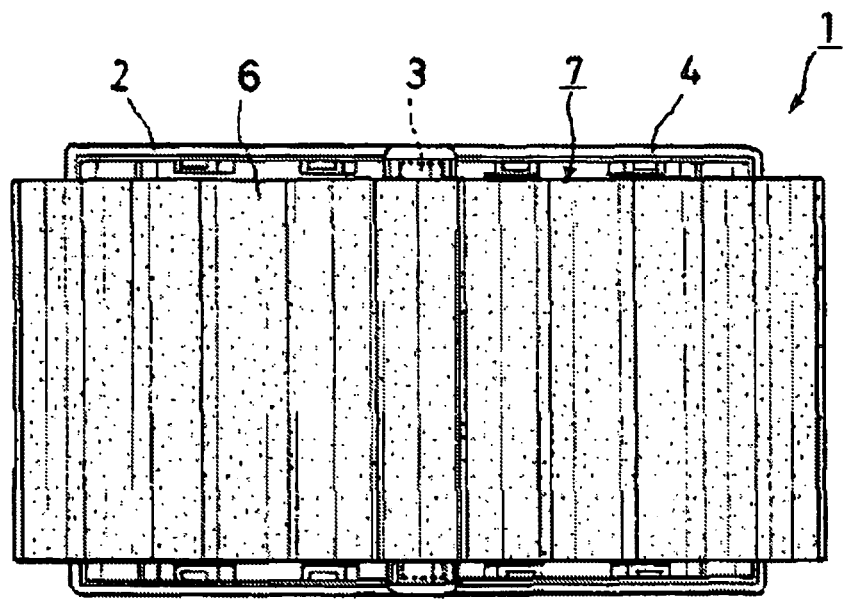
FIG. 1 is a plan view of an open state of a volatilizing apparatus according to a first embodiment of the present invention.

Several embodiments of the present invention will be described hereunder with reference to drawings. In these figures, like elements are given like reference characters.

FIGS. 1 to 9 show a first embodiment of the present invention. A volatilizing apparatus 1 can volatilize a volatile agent. The volatilizing apparatus 1 comprises a container 50 and a volatilizing body 7. The container 50 comprises a container body 2 and a lid 4 covering the container body 2. The container body 2 has a square shape and is formed as a shallow dish. The lid 4 is attached to the container body 2 through a hinge member 3 so as to open and close with respect to the container body 2.

The volatilizing body 7 has a laminated honeycomb structure and holds a volatile agent 6. The volatile agent 6 may be held on the volatilizing body 7 by spraying, coating, impregnation, immersion etc. One of the ends of the volatilizing body 7 is fixed to the inner face of the container body 2 and the other of the ends of the volatilizing body 7 is fixed to the inner face of the lid 4. Both ends of the volatilizing body 7 are fixed by means of an adhesive agent. Incidentally, both ends of the volatilizing body 7 may be fixed detachably by means of an engaging member or a supporting member (not shown). The volatilizing body 7 is adapted to be contained in the container 50 under the closed state of the lid 4 and to expand between the container body 2 and the lid 4 under the open state of the lid 4.

The kind and type of the volatile agents may be selected for use with the volatilizing apparatus. At least one kind of the volatile agents, such as deodorant, aromatic agent, pesticide, insecticide, fungicide, fresh-keeping agent, etc., may be used. And either of two types of the volatile agents may be used. One type of agent is an agent that is volatilized at ordinary temperature and another type of agent is an agent that is volatilized under a hot condition. In order that the volatile agent can be volatilized at the temperature at which the volatilizing apparatus is used, the former type agent does not require that the surrounding ambience of the volatilizing apparatus is heated and the latter type agent requires it. Incidentally, ordinary temperature means room temperature. Room temperature includes also the temperature in a refrigerator or a freezer when the volatilizing apparatus is used in a refrigerator or freezer. In the first embodiment, the volatile agent which is an insecticide and is the former type, is used.

The following agents may be used as a deodorant or an aromatic agent. For example, the agents containing the following components; such as benzaldehyde, α-pinene, geraniol, citronellal, linalool, limonene, menthol linalyl acetate, amyl cinnamic aldehyde, methyl anthranate, isoeugenol, allyl caproate, isobutyl acetate, benzyl acetate, isoamyl salicylate, citral, decyl aldehyde, hydroxy citronellal, isoamyl acetate etc. Essential oil which can diffuse an aroma or eliminate an odor; such as bitter almond oil, hinoki oil, nutmeg oil, geranium oil, lavender oil, lime oil, peppermint oil, vetiver oil, sweet orange oil, thyme oil, etc.

The following agents may be used as the insecticide. For example, the agents containing the following components; such as α-pinene, eugenol, thujone, thymol, hinokitiol, cinnamic aldehyde etc. Essential oil which can repel or kill the insect; such as nutmeg oil, clove oil, sage oil, thyme oil, lavender oil, basil oil, hinoki oil, pyrethroid compound, carbamate compound, organophosphorus compound, DEET (N,N-diethyl-m-toluamide etc.

The following compounds may be used as the pyrethroid compound. For example;
Allethrin (dl-3-allyl-2-methyl-4-oxo-2-cyclopentenyl dl-cis/trans-chrysanthemate),
d-Allethrin (dl-3-allyl-2-methyl-4-oxo-2-cyclopentenyl d-cis/trans-chrysanthemate),
S-Bioallethrin (d-3-allyl-2-methyl-4-oxo-2-cyclopentenyl d-trans-chrysanthemate),
Resmethrin ((5-benzyl-3-fulyl)methyl d-cis/trans-chrysanthemate),
Prallethrin ((+)-2-methyl-4-oxo-3-(2-propinyl)-2-cyclopentenyl (+)-cis/trans-chrysanthemate),
Tetramethrin ((1,3,4,5,6,7-hexahydro-1,3-dioxo-2-isoindolyl)methyl dl-cis/trans-chrysanthemate),
d-Tetramethrin (1,3,4,5,6,7-hexahydro-1,3-dioxo-2-isoindolyl)methyl d-cis/trans-chrysanthemate),
d-Phenotrin (3-phenoxybenzyl d-cis/trans-chrysanthemate),
Permethrin (3-phenoxybenzyl dl-cis/trans-3-(2,2-dichlorovinyl)-2,2-dimethyl-1-cyclopropancarboxylate),
Empenthrin (1-ethynyl-2-methyl-2-pentenyl d-cis/trans-chrysanthemate),
2,3,5,6-tetrafluoro-4-methoxymethylbenzyl 3-(1-propenyl)-2,2-dimethylcyclopropanecarboxylate,
2,3,5,6-tetrafluoro-4-methylbenzyl 3-(1-propenyl)-2,2-dimethylcyclopropanecarboxylate,
2,3,5,6-tetrafluorobenzyl 3-(2,2-dichloroethenyl)-2,2-dimethylcyclopropanecarboxylate,
4-methoxymethyl-2,3,5,6-tetrafluorobenzyl 3-(2-methyl-1-propenyl)-2,2-dimethylcyclopropanecarboxylate,
1-ethynyl-2-methyl-2-pentyl 3-(2,2-dichloroethenyl)-2,2-dimethylcyclopropanecarboxylate etc.

The following compounds may be used as the carbamate compounds. For example, Fenobucarb, Carbaryl, Xylylcarb, Ethiofencarb, Metolcarb, Promecarb, Propoxur etc.

The following compounds may be used as the organophosphorus compounds. For example, Chlorpyriphos, Cyanophos, Diazinon, Dichlorvos, Fenitrothion, Fenthion, Malathion, Pyrimiphos-methyl, Prothiofos, Dioxabenzofos, Tetrachlorvinphos, Trichlorfon, Bromophos, Propetamphos etc.

The following compounds may be used as the fungicide. For example, sodium hypochlorite, ortho-phenylphenol, benzalkonium chloride, zinc naphthenate, alcohol, allyl-isothiocyanate, thymol etc.

The following compounds may be used as the fresh keeping agents. For example, isopropylidene aminooxyacetic acid-2-methoxy-2-oxyethylester, silver thiosulfate, thiosulfato silver complex, allylisothiocyanate, cis-propenyl phosphonic acid etc.

The volatilizing body 7 having the laminated honeycomb structure may be manufactured as follows. First, an adhesive agent is coated in many lines and at even intervals, on a first paper material sheet. A second paper material sheet is laminated and bonded on the first paper material sheet. The adhesive agent is coated on the second paper material sheet in the same manner as on the first paper material sheet, except that each line on the second paper material sheet is shifted by a half-pitch from each line on the first paper material sheet. A third paper material sheet is laminated and bonded on the second paper material sheet. Such coating, laminating, and bonding are repeated to obtain the laminated honeycomb structure having a given thickness. The laminated honeycomb structure is made to hold the volatile agent on it by impregnation etc. Lastly, the laminated honeycomb structure is cut into a given shape by punching out. Cutting by punching out will result in a more decorative volatilizing body since this will allow the laminated honeycomb structure shape to be designed at will.

Figure 7:
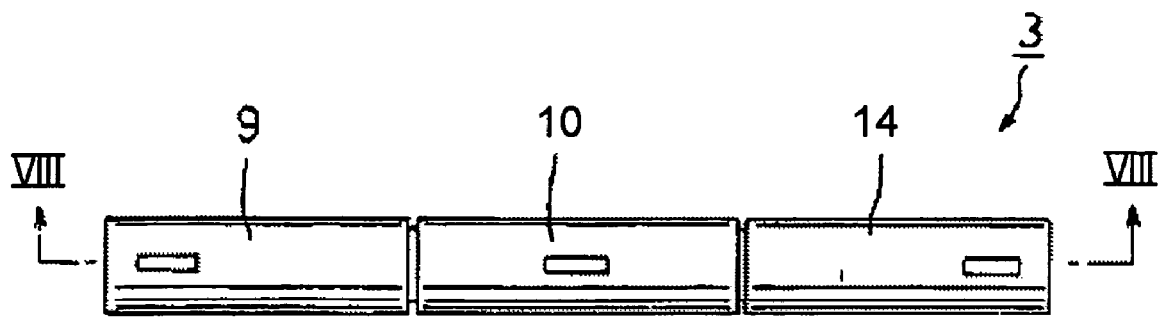
FIG. 7 is a front view of a hinge member of the volatilizing apparatus according to the first embodiment of the present invention.
Figure 8:
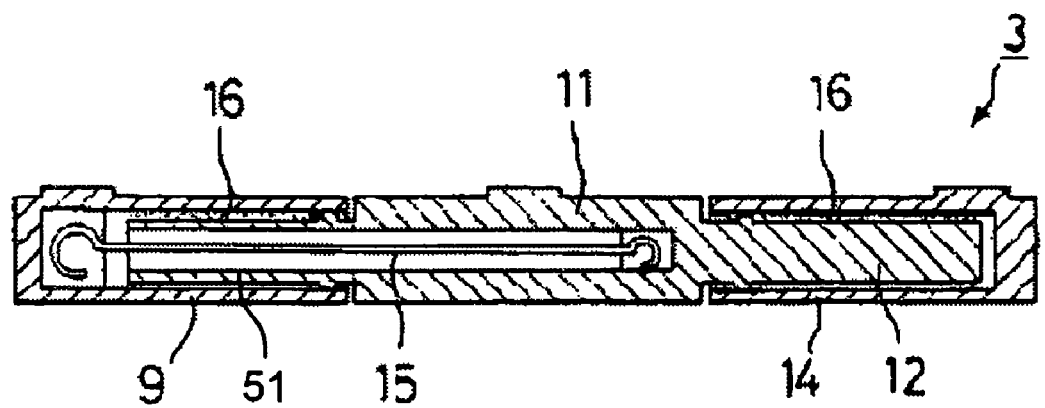
FIG. 8 is a sectional view taken on a line VIII—VIII of FIG. 7.

The hinge member 3 is provided at the rear end of the container 50. As shown in FIGS. 7 & 8, the hinge member 3 includes a rotation axis 11 and a spring 15. The rotation axis 11 is fixed to an attaching part 10 (FIG. 4) of the lid 4. One end part 51 of the rotation axis 11 is inserted rotatably in a case body 9 and the other end part (a support axis 12) of it is inserted rotatably in a support tube 14. If necessary, grease 16 is filled in clearances between the end part 51 and the case body 9, and between the support axis 12 and the support tube 14. The grease 16 can provide resistance against rotating of the end part 51 and the support axis 12.

Figure 2:
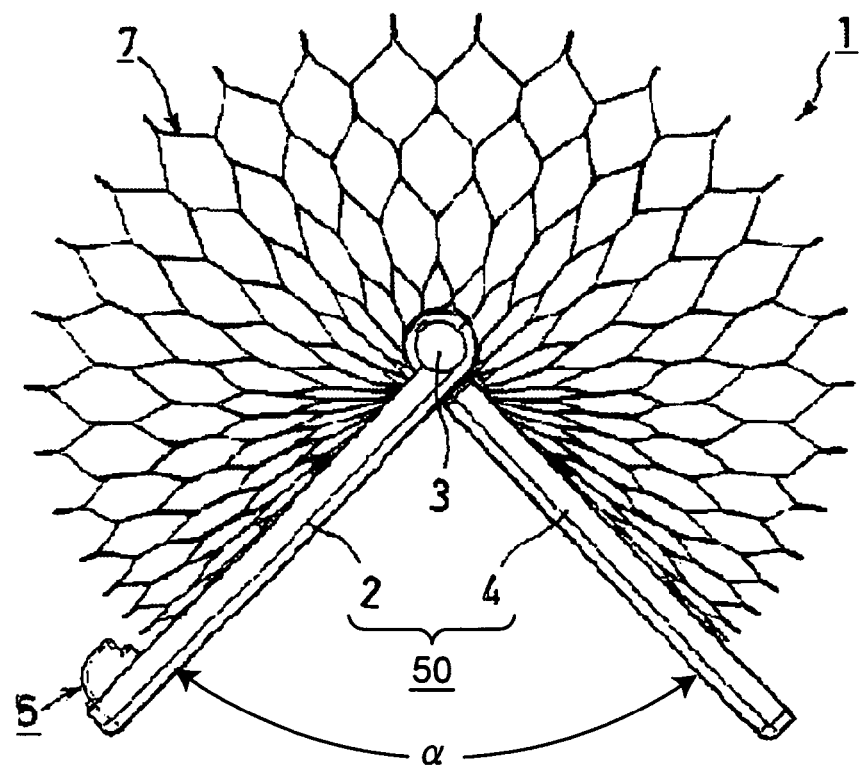
FIG. 2 is a front view of the open state of the volatilizing apparatus according to the first embodiment of the present invention.
Figure 3:
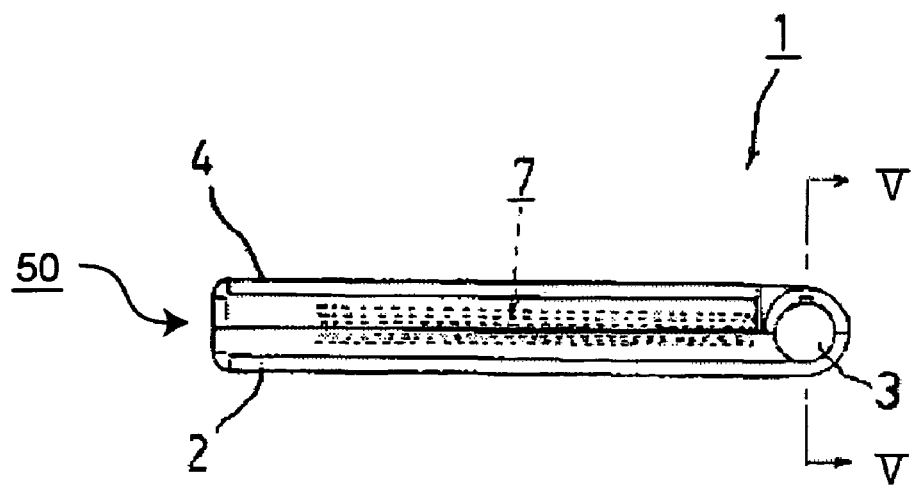
FIG. 3 is a front view of a closed state of the volatilizing apparatus according to the first embodiment of the present invention.
Figure 4:
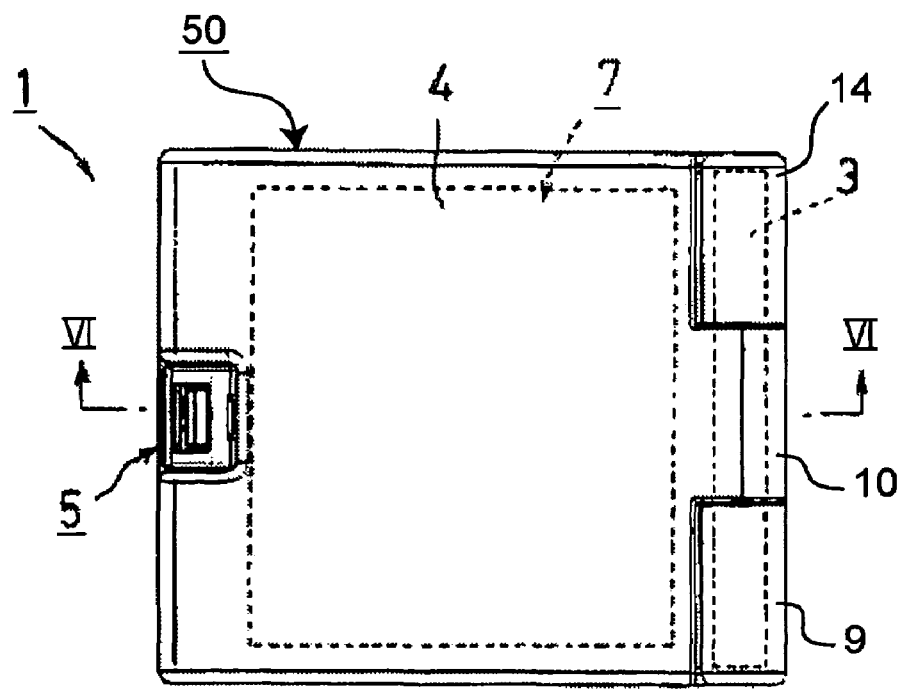
FIG. 4 is a plan view of the closed state of the volatilizing apparatus according to the first embodiment of the present invention.
Figure 5:
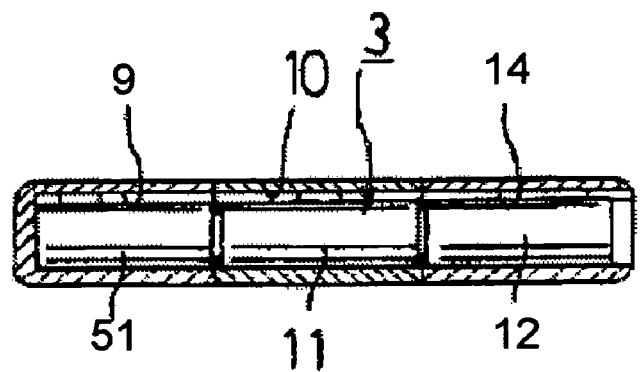
FIG. 5 is a sectional view taken on a line V—V of FIG. 3.
Figure 6:
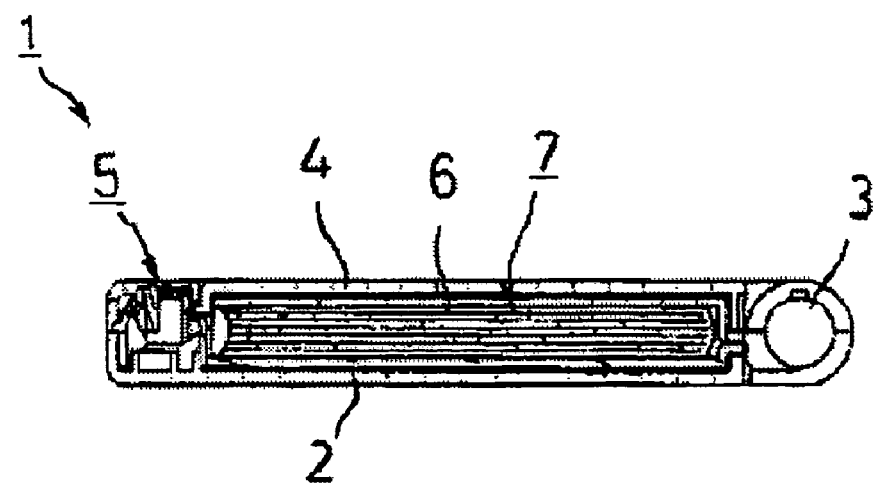
FIG. 6 is a sectional view taken on a line VI—VI of FIG. 4.

The spring 15 is included in the rotation axis 11. One end of the spring 15 is engaged with the inner surface of the case body 9 and the other end of it is engaged with the inside of the rotation axis 11. The spring 15 has an elastic force for energizing the lid 4 in a direction in which it opens from the container body 2. The spring 15 is preferably set to open the lid 4 in a range from 230 degrees to 330 degrees, more preferably from 250 degrees to 310 degrees, with respect to the container body 2. That is, the angle $\alpha$ shown in FIG. 2 is preferably set in a range from 30 degrees to 130 degrees, more preferably from 50 degrees to 110 degrees.

Figure 9:
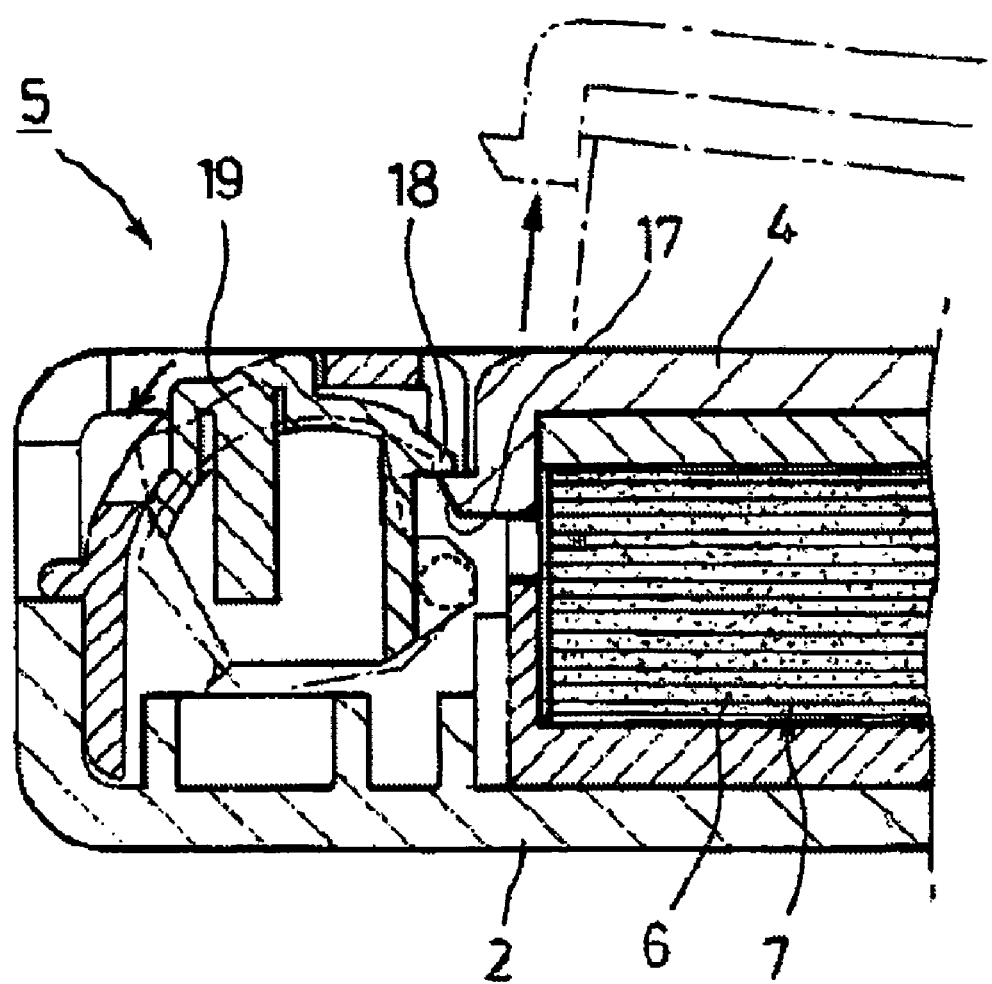
FIG. 9 is a sectional view of a locking tool of the volatilizing apparatus according to the first embodiment of the present invention.

The container 50 includes a locking tool 5 for locking the lid 4 to the container body 2 under the closed state of the container 50. The locking tool 5 comprises a locking piece 17 formed at the lid 4 and an engaging part 18 formed at the container body 2 for engaging with the locking piece 17, as shown in FIG. 9. The locking piece 17 is provided, so as to project downwardly at the under surface of the center part in the front part of the lid 4. The engaging part 18 is provided at a part of the container body 2 corresponding to the locking piece 17. Under the closed state of the container 50, the engaging part 18 is engaged with the locking piece 17. The engaging part 18 is energized by a spring etc. (not shown) in a direction in which it engages with the locking piece 17. The engaging part 18 has an operating part 19 that can be pressed by a user. Pressing the operating part 19 will allow the engaging part 18 to disengage from the locking piece 17.

The volatilizing apparatus 1 is used as follows. First, the volatilizing apparatus 1 is placed at the proper place. The operating part 19 is pressed to disengage the engaging part 18 from the locking piece 17. The lid 4 is energized by means of the hinge member 3 in the direction of opening. Therefore, the lid 4 is opened automatically in a range from 230 degrees to 330 degrees, more preferably from 250 degrees to 310 degrees, with respect to the container body 2. At the same time, the volatilizing body 7 expands automatically in an arc between the container body 2 and the lid 4. In addition, the volatilizing apparatus 1 stands due to the open container body 2, as shown in FIG. 2.

According to the volatilizing apparatus 1 having the composition as described above, the following effects can be obtained.

(1) It is easy for the user to open the container 50 since the lid 4 can be opened automatically. Therefore, the volatilizing apparatus 1 can be handled easily.

(2) Since the volatilizing body 7 expands automatically, the volatilizing apparatus 1 can prevent the user from touching the volatilizing body 7. Therefore, the volatilizing apparatus 1 can be handled safely.

(3) The volatilizing body 7 expands in an arc in a range from 230 degrees to 330 degrees. Therefore, the volatile agent can be volatilized effectively from the volatilizing body 7 since the open area of the volatilizing body 7 becomes large. In addition, the decorative effect of the volatilizing body 7 can be improved.

(4) The volatilizing apparatus 1 stands due to the open container body 2. Therefore, the setting area of the volatilizing apparatus 1 can be made small and the decorative effect of the volatilizing body 7 can be improved.

Incidentally, a slip stopper is preferably provided on the outer surface of at least one of the container body 2 and the lid 4. According to the composition, the volatilizing apparatus 1 can easily stand up. The slip stopper preferably has a high coefficient of friction to the surface of the setting place. For example, a rubber member is preferably used as the slip stopper. A pin, which can prevent the standing volatilizing apparatus 1 from shaking, is preferably provided on the outer surface of at least one of the container body 2 and the lid 4. The pin is more preferably provided together with the slip stopper.

Figure 10:
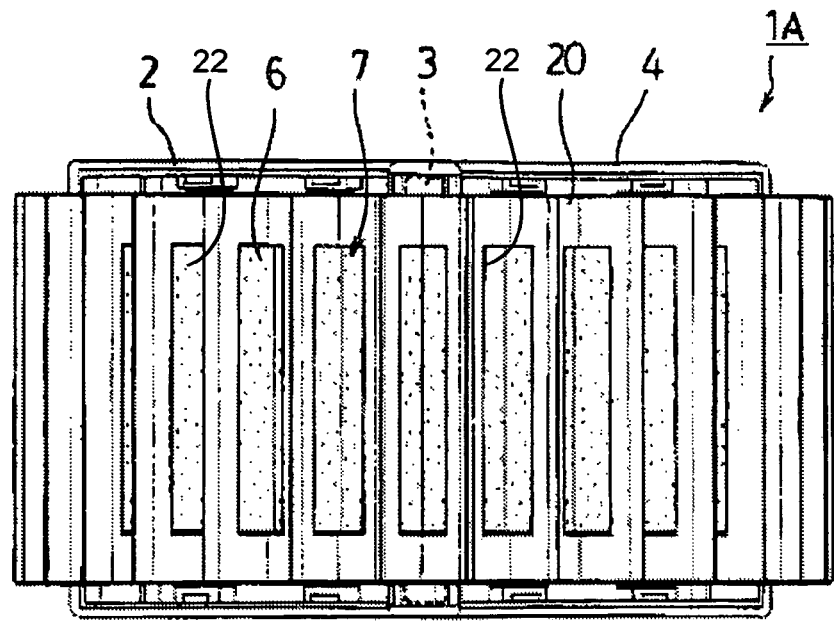
FIG. 10 is a plan view of an open state of a volatilizing apparatus according to a second embodiment of the present invention.
Figure 11:
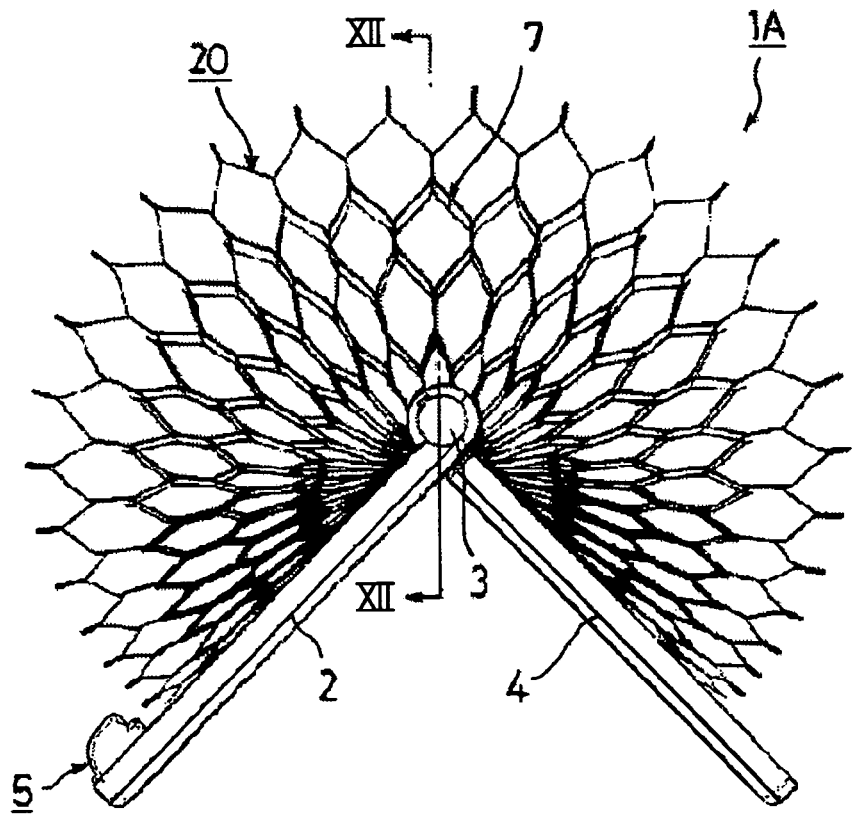
FIG. 11 is a Front view of the open state of the volatilizing apparatus according to the second embodiment of the present invention.
Figure 12:
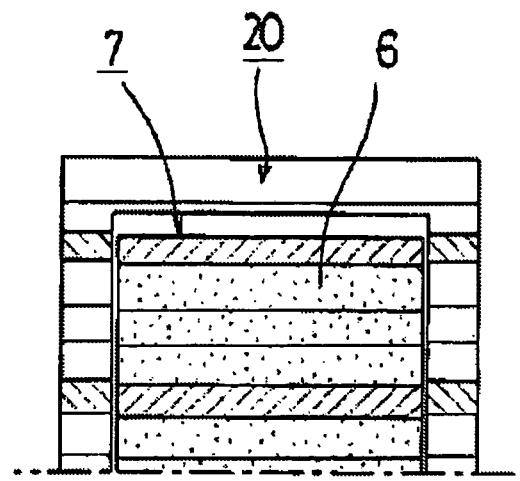
FIG. 12 is a sectional partial view taken on a line XII—XII of FIG. 11.

FIGS. 10 to 12 show a second embodiment of the present invention. A volatilizing apparatus 1A of the second embodiment has the same composition as that of the first embodiment, except that a cover body 20 is provided. The cover body 20 has the laminated honeycomb structure and covers the upper part and both side parts of the volatilizing body 7. Slits 22 are formed at the upper part of the cover body 20.

According to the volatilizing apparatus 1A, the same effects as the first embodiment can be obtained. In addition, the cover body 20 can prevent the user from touching the volatilizing body 7. Therefore, the volatilizing apparatus 1A can be handled more safely. The color of the cover body 20 is preferably different from that of the volatilizing body 7. In addition, the upper part of the volatilizing body 7 can be seen through the slits 22. According to it, the decorative effect can be improved.

It is preferred that the volatilizing body 7 is made of a material having a high capability of holding the volatile agent, and that the cover body 20 is made of a material having a high capability of maintaining its style (i.e. hard).

Figure 13:
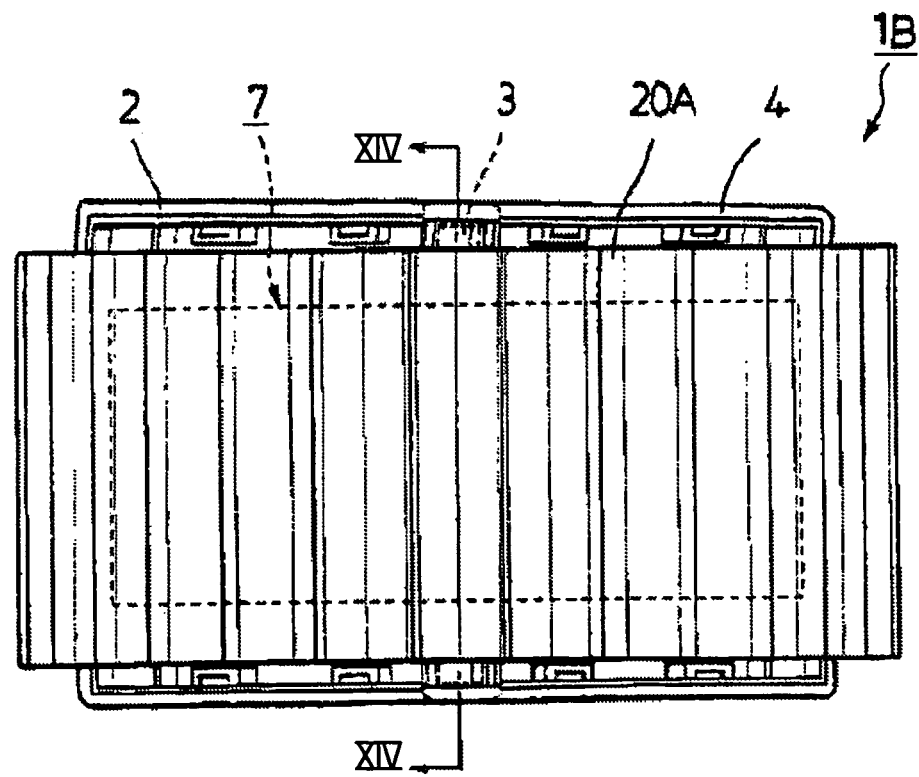
FIG. 13 is a plan view of an open state of a volatilizing apparatus according to a third embodiment of the present invention.
Figure 14:
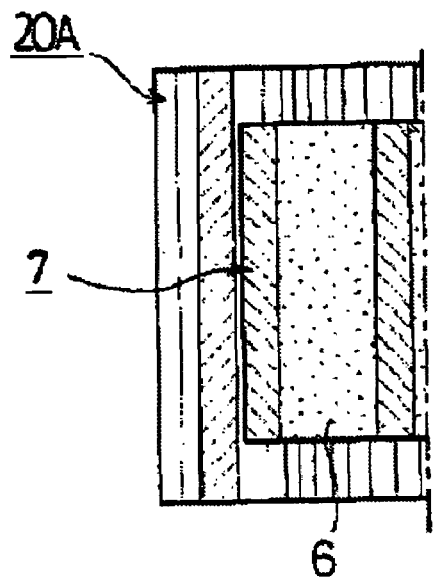
FIG. 14 is a sectional partial view taken on a line XIV—XIV of FIG. 13.

FIGS. 13 and 14 show a third embodiment of the present invention. A volatilizing apparatus 1B of the third embodiment has the same composition as that of the second embodiment, except that a cover body 20A is provided. The cover body 20A of the third embodiment and the cover body 20 of the second embodiment are different only in that the cover body 20A has no slits 22 and completely covers the upper part of the volatilizing body 7.

Figure 15:
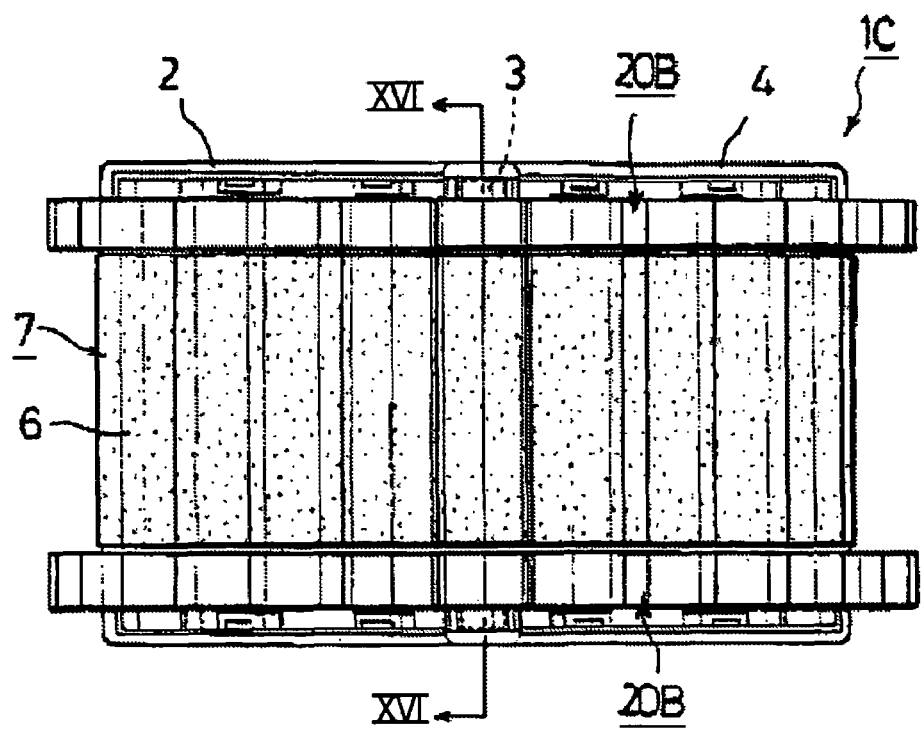
FIG. 15 is a plan view of an open state of a volatilizing apparatus according to a fourth embodiment of the present invention.
Figure 16:
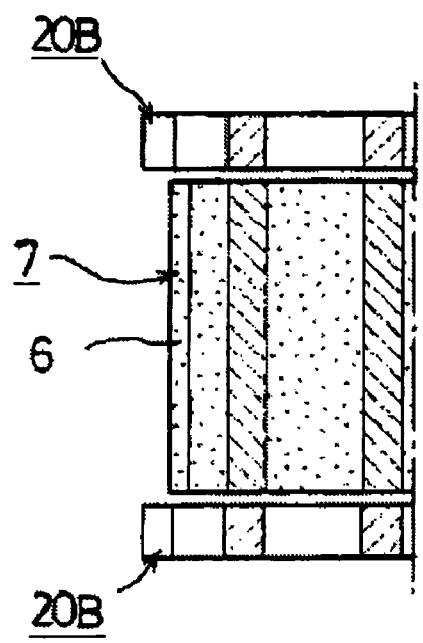
FIG. 16 is a sectional partial view taken on a line XVI—XVI of FIG. 15.

FIGS. 15 and 16 show a fourth embodiment of the present invention. A volatilizing apparatus 1C of the fourth embodiment has the same composition as that of the second embodiment, except that two cover bodies 20B, 20B are provided. The cover body 20B of the fourth embodiment and the cover body 20 of the second embodiment are different only in that the cover body 20B covers only the side part of the volatilizing body 7. The two cover bodies 20B, 20B cover both side parts of the volatilizing body 7.

Figure 17:
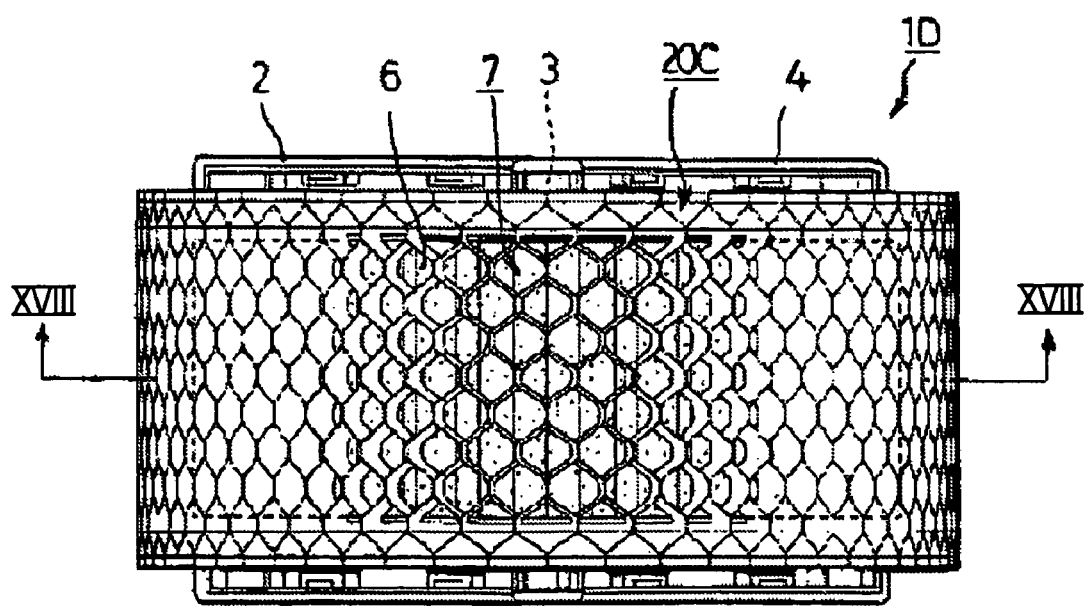
FIG. 17 is a plan view of an open state of a volatilizing apparatus according to a fifth embodiment of the present invention.
Figure 18:
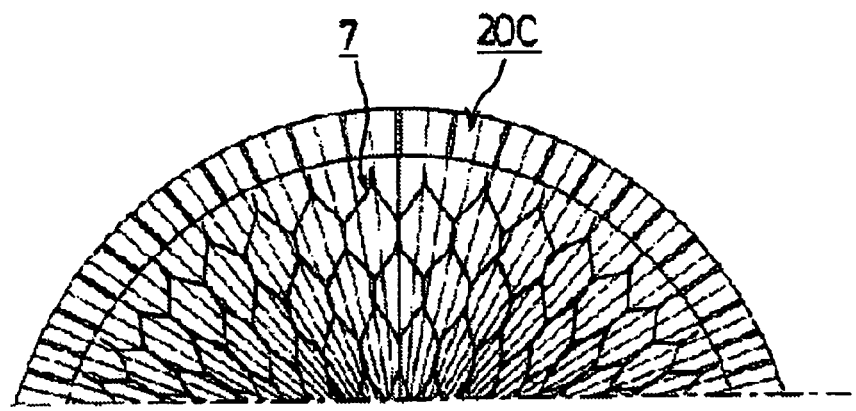
FIG. 18 is a sectional partial view taken on a line XVIII—XVIII of FIG. 17.

FIGS. 17 and 18 show a fifth embodiment of the present invention. A volatilizing apparatus 1D of the fifth embodiment has the same composition as that of the third embodiment, except that a cover body 20C is provided. The cover body 20C of the fifth embodiment and the cover body 20A of the third embodiment are different only in the laminated honeycomb structure. The laminated honeycomb structure of the cover body 20C is different from that of the volatilizing body 7, as shown in FIG. 18. Incidentally, the laminated honeycomb structure of the volatilizing body 7 in FIG. 18 may be exchanged for the laminated honeycomb structure of the cover body 20C in FIG. 18.

Figure 19:
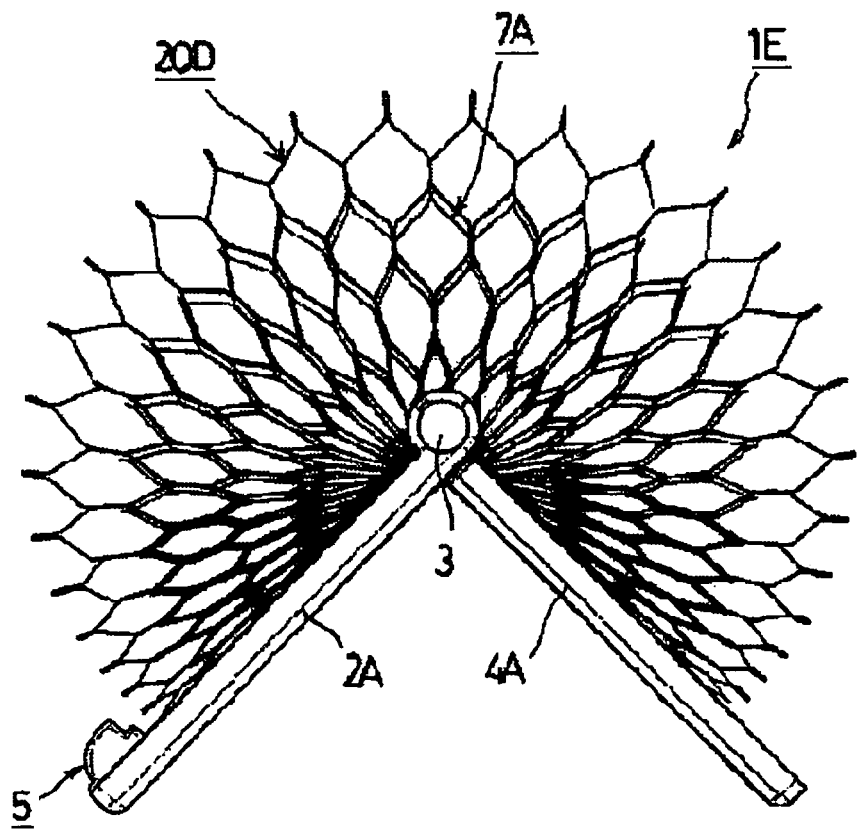
FIG. 19 is a front view of an open state of a volatilizing apparatus according to a sixth embodiment of the present invention.
Figure 20:
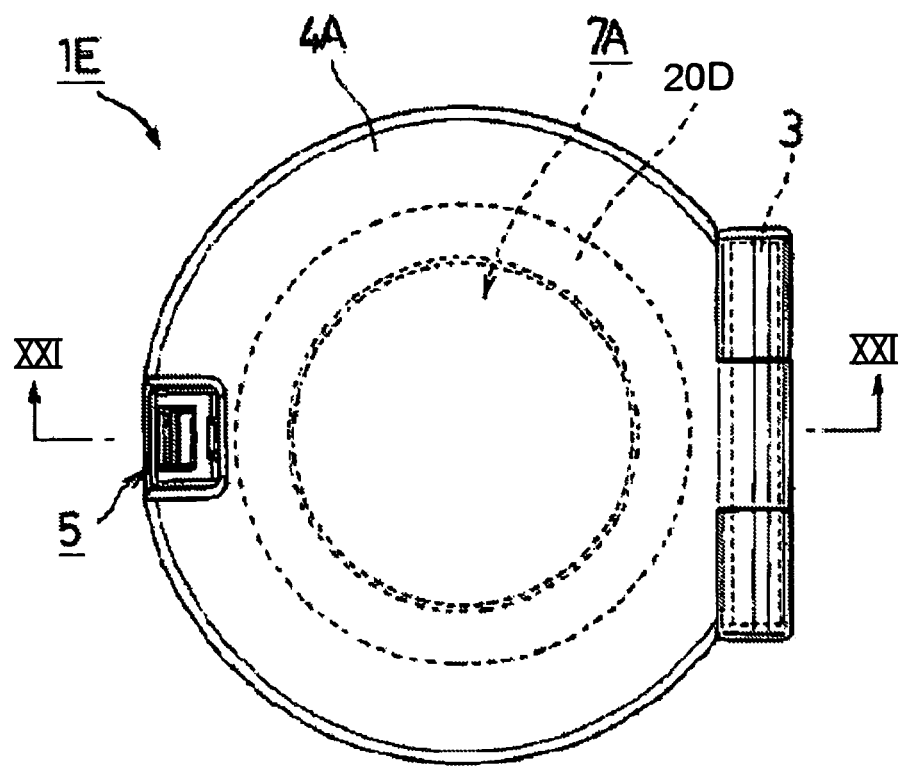
FIG. 20 is a plan view of a closed state of the volatilizing apparatus according to the sixth embodiment of the present invention.
Figure 21:
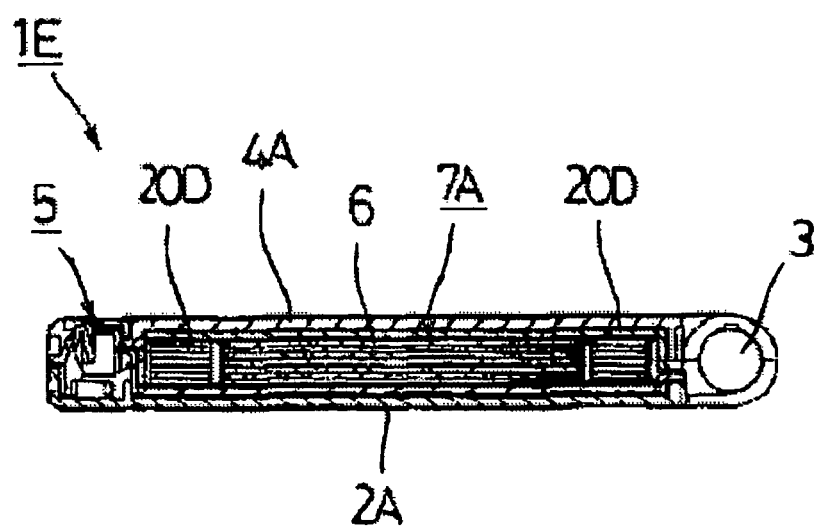
FIG. 21 is a sectional view taken on a line XXI—XXI of FIG. 20.

FIGS. 19 to 21 show a sixth embodiment of the present invention. The volatilizing apparatus 1E of the sixth embodiment has the same composition as that of the third embodiment, except that a container body 2A, a lid 4A, and a volatilizing body 7A have circular forms in the plan view and a cover body 20D has a ring form in the plan view. Incidentally, instead of the circular form or the ring form, a triangular form, a square form, an infinite form, etc. may be adopted.

In the volatilizing apparatus of the present invention, the following compositions may be employed.

(1) The container 50 may contain several volatilizing bodies. In that case, each of the volatilizing bodies may hold a different volatile agent. For example, one of the volatilizing bodies may hold the aromatic agent and another of the volatilizing bodies may hold the deodorant.

(2) The container 50 may contain several volatilizing bodies. In that case, the arrangement of the volatilizing bodies can be set at will.

For example, they are arranged inside and outside. This arrangement can use different volatile agents, each of which has a different volatility. It is preferred that the outside volatilizing body holds the volatile agent that is less volatile and the inside volatilizing body holds the volatile agent that is more volatile. According to this arrangement, all volatilization can be completed simultaneously.

(3) The composition of the hinge member of the present invention is not limited to that of the hinge member 3. A coil spring, a torsion bar, a hydraulic mechanism, a pneumatic mechanism, etc. which can energize the lid 4 so that the lid 4 opens in a range from 230 degrees to 330 degrees with respect to the container body 2, may be adopted as the composition of the hinge member.

The hinge member may comprise a hinge part formed in a joint or a thin part and an energizing mechanism for energizing the lid 4 so that the lid 4 opens in a range from 230 degrees to 330 degrees with respect to the container body 2.

(4) The volatile agent which is volatilized in a hot condition may be used. In that case, it is preferred that the volatilizing apparatus includes a heating means. For example, a heating element, such as a disposable body warmer that is commercially available and utilizes the heat derived from the oxidation of iron powder, may be attached to the container body 2.

What is claimed is:

1. A volatilizing apparatus for volatilizing a volatile agent, comprising:
    a container comprising a container body and a lid covering said container body, said lid being attached to said container body through a hinge member so as to open and close with respect to said container body; and
    a volatilizing body having first and second ends, said first end of said volatilizing body being fixed to an inner face of said container body, and said second end of said volatilizing body fixed to an inner face of said lid, said volatilizing body having a laminated honeycomb structure, holding said volatile agent, and being adapted to be contained in said container under a closed state of said lid and to expand between said container body and said lid under an open state of said lid;
    wherein said hinge member includes an energizing means for energizing said lid in a direction in which it opens from said container body, and
    wherein said container includes a locking tool for locking said lid in said closed state to said container body.

2. The volatilizing apparatus according to claim 1, wherein said energizing means is set to open said lid in a range from 230 degrees to 330 degrees with respect to said container body.

3. The volatilizing apparatus according to claim 1, wherein said locking tool comprises a locking piece formed at said lid and an engaging part formed at said container body for engaging with said locking piece, and
    wherein said engaging part is adapted to disengage said locking piece from an engaged state by being pressed.

4. The volatilizing apparatus according to claim 1, wherein said volatile agent is at least one selected from deodorant, aromatic agent, insecticide, pesticide, fungicide, and fresh-keeping agent.

5. The volatilizing apparatus according to claim 1, wherein said volatilizing body is provided with a cover body, said cover body having a laminated honeycomb structure and covering an upper part or a side part of said volatilizing body.

6. A volatilizing apparatus for volatilizing a volatile agent, comprising:
    a container comprising a container body and a lid covering said container body, said lid being attached to said container body through a hinge member so as to open and close with respect to said container body; and
    a volatilizing body having first and second ends, said first end of said volatilizing body being fixed to an inner face of said container body, and said second end of said volatilizing body being fixed to an inner face of said lid, said volatilizing body having a laminated honeycomb structure, holding said volatile agent, and being adapted to be contained in said container under a closed state of said lid and to expand between said container body and said lid under an open state of said lid;
    wherein said hinge member includes a spring installed so as to store an elastic force in said closed state of said lid for energizing said lid in a direction in which it opens from said container body, and
    wherein said container includes a locking tool for locking said lid in said closed state to said container body.

7. The volatilizing apparatus according to claim 6, wherein said spring installed so as to store an elastic force in said closed state of said lid is set to open said lid in a range from 230 degrees to 330 degrees with respect to said container body.

8. The volatilizing apparatus according to claim 6, wherein said locking tool comprises a locking piece formed at said lid and an engaging part formed at said container body for engaging with said locking piece, and wherein said engaging part is adapted to disengage said locking piece from an engaged state by being pressed.

9. The volatilizing apparatus according to claim 6, wherein said volatile agent is at least one selected from deodorant, aromatic agent, insecticide, pesticide, fungicide, and fresh-keeping agent.

10. The volatilizing apparatus according to claim 6, wherein said volatilizing body is provided with a cover body, said cover body having a laminated honeycomb structure and covering an upper part or a side part of said volatilizing body.

\* \* \* \* \*